US00PP25826P2

(12) United States Plant Patent
Kordes

(10) Patent No.: US PP25,826 P2
(45) Date of Patent: Aug. 25, 2015

(54) HYBRID TEA ROSE PLANT NAMED 'KORTRINKA'

(50) Latin Name: *Rosa hybrida*
Varietal Denomination: KORtrinka

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes' Sohne Rosenschulen GmbH & Co KG, Offenseth-Sparrieshoop (DE)

( * ) Notice: Subject to any disclaimer, the term of this patent is extended or adjusted under 35 U.S.C. 154(b) by 184 days.

(21) Appl. No.: 13/987,443

(22) Filed: Jul. 24, 2013

(51) Int. Cl.
*A01H 5/02* (2006.01)

(52) U.S. Cl.
USPC ..... Plt./139

(58) Field of Classification Search
USPC ..... Plt./139, 140
See application file for complete search history.

(56) References Cited

PUBLICATIONS

Gabot Dossier: IPM 2013 Kordes Roses, Jun. 12, 2012, 3 pp.*
HelpMeFind Roses, Clematis and Peonies and everything gardening related. Kortrinka Rose Description 2015, retrieved on Mar. 17, 2015, retrieved from the Internet at <www.helpmefind.com/rose/pl.php?n=93659>, one page.*
Upov Pluto Plant Variety Database 20150316, retrieved on Mar. 17, 2015, retrieved from the Internet at <www.wipo.int/pluto/user/en/index.jsp> one page.*
Gabot Dossier: IPM 2013 English translation 3 pp.*

* cited by examiner

*Primary Examiner* — June Hwu

(57) ABSTRACT

A new and distinct variety of rose with long lasting, novel red flowers, and attractive foliage with very good disease resistance. It exhibits upright to busy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORtrinka'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 2000. The crossing was between an 'un-named seedling', the seed parent, and another 'un-named seedling', the pollen parent by the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORtrinka'.

SUMMARY OF THE INVENTION

The new rose plant may be distinguished from its seed parent, an 'un-named seedling', by the following combination of characteristics:

1. 'KORtrinka' has red flowers, whereas the 'un-named seedling' has salmon pink flowers.
2. 'KORtrinka' has a double petal count, whereas the 'un-named seedling' has a semi-double petal count.

The new rose plant may be distinguished from its pollen parent, an 'un-named seedling', by the following combination of characteristics:

1. 'KORtrinka' has very good disease resistance, whereas the 'un-named seedling' has poor disease resistance.
2. 'KORtrinka' has red flowers, whereas the 'un-named seedling' has dark red flowers.

The objective of the hybridization was to create a new and distinct rose plant with unique qualities, such as:

1. Uniform growth and flowering;
2. Abundant attractive, recurrent flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORtrinka' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORtrinka' was selected in May 2001 from the seedling beds to be asexually propagated for further evaluation. The first asexual propagation of 'KORtrinka' was done by budding in July 2001 at the inventor's nursery in Offenseth-Sparrieshoop, Germany.

These initial and other subsequent propagations conducted in controlled environments demonstrate that 'KORtrinka' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORtrinka' taken from plants of 5 years of age.

DETAILED BOTANICAL DESCRIPTION

The following is a description of 'KORtrinka', as observed growing in June 2013 in a nursery in Jackson County, Oreg. on plants of 5 years of age. Color references are made using The Royal Horticultural Society (London, England) Colour Chart, 2001 except where common terms of color are used.

For a comparison, several physical characteristics of the rose variety 'KORtrameilo', a rose variety from the same inventor described and illustrated in U.S. Plant Pat. No. 24,196 and issued on Jan. 28, 2014 are compared to 'KORtrinka' in Chart 1.

CHART 1

| Characteristic | 'KORtrinka' | 'KORtrameilo' |
|---|---|---|
| Bud form | Pointed ovoid | Globular |
| Petal count | Double (approx. 35) | Very double (approx. 70) |
| Plant habit | Upright to bushy | Upright climbing |

Parents:

*Seed parent*.—An 'un-named seedling'.

*Pollen parent*.—An 'un-named seedling'.

Classification:

*Botanical classification*.—*Rosa hybrida* 'KORtrinka'.

*Commercial classification*.—Hybrid Tea rose.

FLOWER AND FLOWER BUD

*Blooming habit*.—Continuous.

*Flower bud*.—Size: Upon opening, 25-30 mm in length from base of receptacle to distal end of bud and 15-18 mm diameter at its widest point. Bud form: Short. Pointed ovoid. Bud color: As sepals first unfold, bud color is Greyed-Purple Group 187A to Greyed-Purple Group 187C. When ¼ open, the upper surface of petals is Red Group 46B to Red Group 45A, and the lower surface is Red Group 53C. Upper surface of guard petals are Red Group 45B, most commonly with a center stripe of Green-White Group 157B. Lower surface of guard petals is Red Group 53C with an occasional stripe of Green-White Group 157B. Sepals: Color: Upper surface Yellow-Green Group 144B. Lower surface Yellow-Green Group 144A. Intonations of Greyed-Purple Group 183A present on upper and lower surfaces. Size: Average 28 mm (l)× 10-12 mm (w). Shape: Moderately strong foliaceous appendages on 3 of the five sepals. Apex: Somewhat cirrose. Base: Flat at union with receptacle. Quantity: Five. Surface texture: Upper side: Abundant pubescence present. Lower surface: A few stipitate glands present. Margins: With fine hairs and stipitate glands.

*Flower bloom*.—Fragrance: Light. Duration: On the plant 4-5 days. As a cut flower, 3 days. Senesced petals clinging. Size: Medium for a hybrid tea rose. When open, the average flower diameter is 85-95 mm and the average flower height is 40-45 mm. Form: Shape of flower when viewed from the side: Upon opening, upper part: Flat. Upon opening, lower part: Concave. Open flower, upper part: Flat. Open flower, lower part: Concave to flattened convex.

*Color*.—Upon opening, petals: Outermost petals: Outer Side: Red Group 53C. Inner Side: Red Group 46B. Innermost petals: Outer Side: Red Group 53C. Inner Side: Red Group 45B. Upon opening, basal petal spots: Basal petal spot, outermost petals: Outer Side: Green-Yellow Group 1A. Inner Side: Yellow Group 4A. Basal petal spot, innermost petals: Outer Side: Yellow-Orange Group 15A. Inner Side: Yellow-Orange Group 17C. After opening, petals: Outermost petals: Outer Side: Red Group 53C. Inner Side: Red Group 45B. Innermost petals: Outer Side: Red Group 53C. Inner Side: Red Group 45B. After opening, basal petal spots: Basal petal spot, outermost petals: Outer Side: Green-Yellow Group 1A. Inner Side: Yellow Group 4A. Basal petal spot, innermost petals: Outer Side: Yellow Group 4A. Inner Side: Yellow-Orange Group 14B.

General tonality: On open flower Red Group 45B. No change in the general tonality at the end of the 3$^{rd}$ day. Afterwards, general tonality is Red-Purple Group 64B to Red-Purple Group N66A.

Petals:

*Petal count*.—Double.

*Average range*.—Approximately 35 petals under normal conditions.

*Petal reflex*.—Petals reflex slightly.

*Petal margin*.—Somewhat undulated.

*Petal incisions*.—One incision typically present at petal apex.

*Petal shape*.—Obovate. Apex: Obtuse. Base: Cuneate.

*Petal size*.—40-48 mm (l)×45-50 mm (w).

*Thickness*.—Average.

*Petal arrangement*.—Not formal.

*Texture*.—Smooth.

Petaloids:

*Petaloid count*.—Average of 10-12 per flower.

*Petaloid size*.—18-30 mm (l)×12-25 mm (w).

*Petaloid color*.—Inner side: Red Group 46C. Outer side: Red Group 53D.

*Petaloid texture*.—Smooth.

*Margins*.—Mostly entire to incised.

*Petaloid shape*.—Most commonly obovate with some petaloids highly irregular. Apex: Obtuse. Base: Cuneate to attenuate.

Reproductive organs:

*Pistils*.—Abundant. Approximately 80-85 present. Stigmas: Location: Slightly inferior in position to anthers. Color: Greyed-Yellow Group 160C. Styles: Length: About 5-7 mm long. Color: Green-White Group 157D. Intonations: Red-Purple Group N66A.

*Stamens*.—Approximately 80-85 on average and regularly arranged. Anthers: Size: Average 3-4 mm (l)×1.5 mm (w). Color: Greyed-Yellow Group 161 D. Pollen:

Generally present. Color: Greyed-Orange Group 163B. Filaments: Color: Greyed-Orange Group N163C. Length: 10 mm.

*Receptacle*.—Surface: With a few fine hairs. Color: Yellow-Green Group 144A to Yellow-Green Group 144B. Intonations of Greyed-Purple Group 183A. Shape: Urn-shaped. Texture: Smooth. Size: 8-10 mm (h)×10-12 mm (w).

*Peduncle*.—Surface: With fine hairs//and//stipitate glands. Length: 65-70 mm average length. Diameter: 3.5-4 mm average diameter. Color: Yellow-Green Group 144A to Yellow-Green Group 146B. Intonations of Greyed-Purple Group 183A with anthocyanin covering 60-80% of peduncle. Strength: Somewhat strong. Texture: Smooth. Borne: Mostly singular. Occasionally 1-4 flower buds per stem. Flowers upright to slightly pendant.

THE PLANT

*Growth*.—Moderately vigorous.

*Plant habit*.—Upright to bushy. When grown as a field plant, the average plant height is 120 cm and the average plant width is 70-75 cm.

*Stems*.—Stem color: Young wood: Yellow-Green Group 144A. Older wood: Yellow-Green Group 146B. Intonations: Greyed-Purple Group 183A. Anthocyanin covering majority of stem. Stem surface texture: Young wood: Smooth. Older wood: Smooth.

*Prickles*.—Present. Incidence: Average of 5-8 per each 10 cm of stem. Size: Average length: 6-8 mm. Color: Immature prickles: Greyed-Purple Group 183B. Mature prickles: Greyed-Orange Group 165C. Shape: Concave to deeply concave. Anthocyanin: Color Greyed-Orange Group 176C.

*Leaves*.—Normally 5 leaflets on normal leaves in middle of the stem. Venation pattern: Pyramidal net pattern. Leaf size: 145 mm (l)×110 mm (w). Abundance: Average.

*Leaflets*.—Size: Average size of the terminal leaflet is 55-60 mm (l)×45 mm (w). Shape: Elliptic to round. Base: Obtuse. Apex: Acute to apiculate. Margins: Serrated. Undulated. Surface: Upper side of leaflet: Semi-glossy. Lower side of leaflet: Matte. Texture: Upper side of leaflet: Smooth. Under side of leaflet: Smooth. Color, mature foliage: Upper Leaflet Surface: Green Group 137A. Lower Leaflet Surface: Green Group 138B. Color, juvenile foliage: Upper Leaflet Surface: Green Group 137B. Lower Leaflet Surface: Yellow-Green Group 146C. Anthocyanin intonation: Greyed-Purple Group 183A. Location: Lower surface and margin of upper surface of juvenile foliage. Arrangement: Odd pinnate. Venation: Reticulate.

*Stipules*.—Size: 30-35 mm (l)×6-7 mm (w). Stipule color: Yellow-Green Group 146D. Anthocyanin: Greyed-Purple Group 183A. Stipitate glands: Moderately to abundantly present on margins. Texture: Smooth. Shape: Apex: Apiculate. Base: Winged to flat.

*Petiole*.—Length: Average 15-20 mm. Diameter: Average 1 mm. Petiole color: Yellow-Green Group 146B. Underneath: Yellow-Green Group 146C. Margins: With limited numbers of stipitate glands. Anthocyanin: Greyed-Purple Group 183A. Prickles: None observed. Texture: Smooth.

*Petiole rachis*.—Length: Average 45-50 mm. Diameter: Average 1.5 mm. Color: Yellow-Green Group 146B. Anthocyanin present on juvenile tissue: Greyed-Purple Group 183A. Prickles: Generally lacking. Stipitate glands: Limited number of stipitate glands on margins. Texture: Smooth.

Hips/seed formation: None observed.

Winter hardiness: To date, the variety has been grown successfully in Zone 6.

Disease resistance: Very good resistance to Powdery mildew (*Sphaerotheca pannosa*) and blackspot (*Diplocarpon rosae*) diseases under normal growing conditions in Jackson County, Oreg.

I claim:

1. A new and distinct variety of rose plant, as described and illustrated herein.

* * * * *

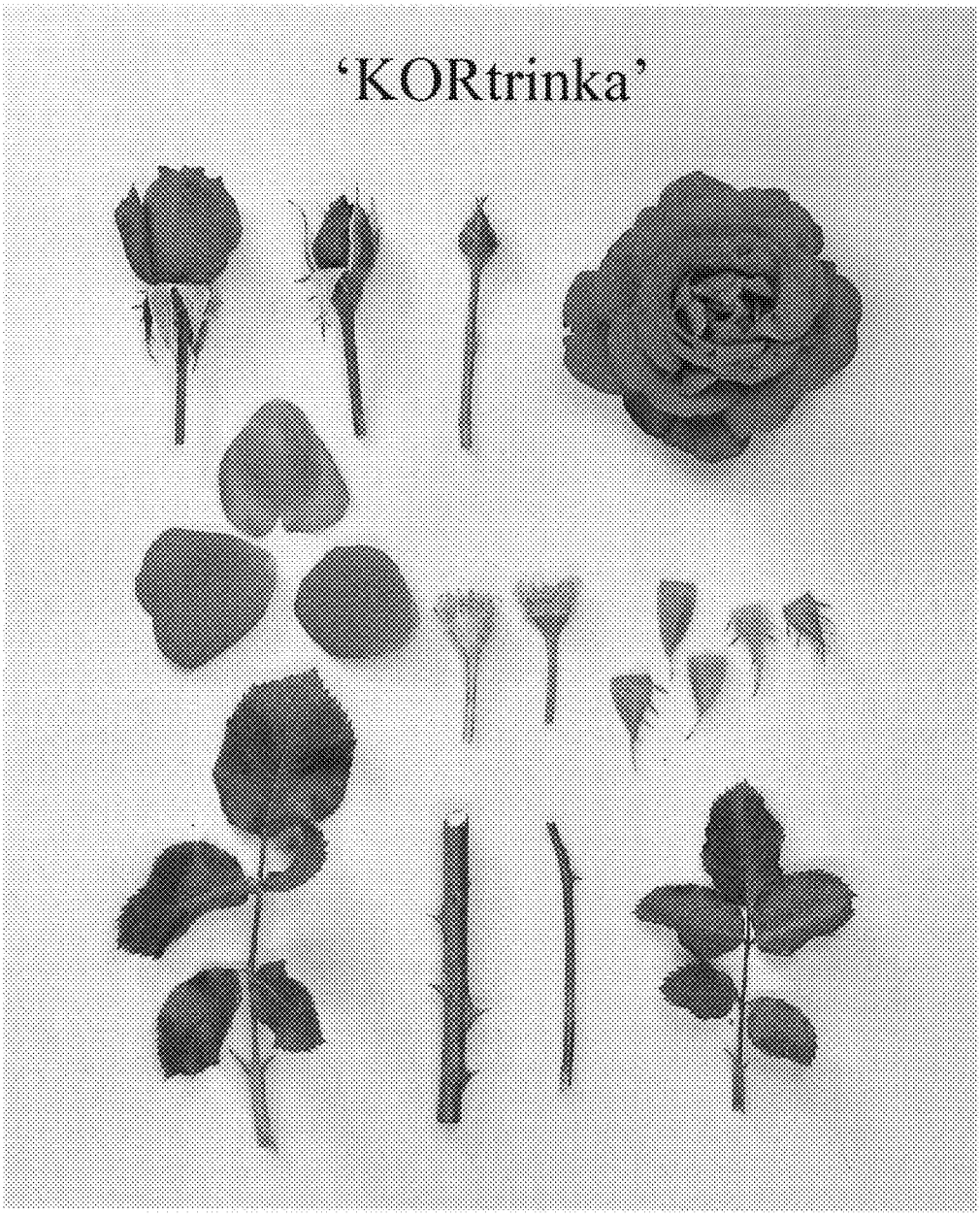
'KORtrinka'